(12) United States Patent
Xu et al.

(10) Patent No.: US 10,527,525 B2
(45) Date of Patent: Jan. 7, 2020

(54) METHOD AND SYSTEM FOR FAST INSPECTING VEHICLE BASED ON MEASURE LENGTHS

(71) Applicant: Nuctech Company Limited, Beijing (CN)

(72) Inventors: Yanwei Xu, Beijing (CN); Weifeng Yu, Beijing (CN)

(73) Assignee: Nuctech Company Limited, Beijing (CN)

(*) Notice: Subject to any disclaimer, the term of this patent is extended or adjusted under 35 U.S.C. 154(b) by 0 days.

(21) Appl. No.: 16/416,934

(22) Filed: May 20, 2019

(65) Prior Publication Data

US 2019/0301976 A1 Oct. 3, 2019

Related U.S. Application Data

(62) Division of application No. 15/278,435, filed on Sep. 28, 2016, now Pat. No. 10,337,960.

(30) Foreign Application Priority Data

Dec. 4, 2015 (CN) .......................... 2015 1 0884071

(51) Int. Cl.
*G01M 17/007* (2006.01)
*G01V 5/00* (2006.01)
(Continued)

(52) U.S. Cl.
CPC ........... *G01M 17/007* (2013.01); *G01B 11/04* (2013.01); *G01N 23/04* (2013.01); *G01V 5/0016* (2013.01);
(Continued)

(58) Field of Classification Search
CPC ..... G01M 17/007; G01B 11/04; G01N 23/04; G01N 2223/631; G01N 2223/03;
(Continued)

(56) References Cited

U.S. PATENT DOCUMENTS 6,507,025 B1  1/2003  Verbinski et al.
9,036,779 B2  5/2015  Morton
(Continued)

FOREIGN PATENT DOCUMENTS

CN  102105815 A  6/2011
CN  102834738 A  12/2012
(Continued)

OTHER PUBLICATIONS

Extended European Search Report dated Apr. 13, 2017 received in European Application No. 16 19 1235.7.
(Continued)

*Primary Examiner* — Michael P LaPage
(74) *Attorney, Agent, or Firm* — Scully Scott Murphy & Presser

(57) ABSTRACT

A method and a system for fast inspecting a vehicle based on a length measuring device, including: when a subject vehicle enters an inspection region, measuring a first length and a second length of the subject vehicle; determining whether the first length and the second length is respectively larger than or equal to a preset second length threshold; if so, determining whether a gap portion of the subject vehicle between a first portion and a second portion of the subject vehicle appears in a beam emitting region formed by a beam of radiation rays emitted by the system for fast inspecting a vehicle; and when the gap portion appears in the beam emitting region, emitting a beam of radiation rays of a first radiation dose to the subject vehicle according to the gap portion, wherein the subject vehicle moves with respect to the system for fast inspecting a vehicle.

10 Claims, 5 Drawing Sheets

(51) Int. Cl.
*G01B 11/04* (2006.01)
*G01N 23/04* (2018.01)

(52) U.S. Cl.
CPC ....... *G01V 5/0066* (2013.01); *G01N 2223/03* (2013.01); *G01N 2223/05* (2013.01); *G01N 2223/631* (2013.01)

(58) Field of Classification Search
CPC ............. G01N 2223/05; G01V 5/0066; G01V 5/0016; G01V 5/0008
See application file for complete search history.

(56) References Cited

U.S. PATENT DOCUMENTS

| | | | |
|---|---|---|---|
| 2005/0169421 A1* | 8/2005 | Muenchau | G01N 23/04 378/57 |
| 2007/0280416 A1* | 12/2007 | Bendahan | G01N 23/04 378/57 |
| 2010/0177873 A1 | 7/2010 | Chen et al. | |
| 2011/0176660 A1* | 7/2011 | Morton | G01V 5/0066 378/57 |
| 2011/0274242 A1 | 11/2011 | Linev | |
| 2013/0039462 A1 | 2/2013 | Morton | |
| 2014/0034829 A1 | 11/2014 | Jeck et al. | |
| 2014/0348295 A1 | 11/2014 | Jeck et al. | |
| 2015/0234082 A1 | 8/2015 | Stoian et al. | |

FOREIGN PATENT DOCUMENTS

| | | |
|---|---|---|
| CN | 103984035 A | 8/2014 |
| CN | 104374785 A | 2/2015 |
| CN | 104391338 A | 3/2015 |
| CN | 104391339 A | 3/2015 |
| CN | 104777520 A | 7/2015 |
| CN | 104950338 A | 9/2015 |
| CN | 105022095 A | 11/2015 |
| CN | 105333826 A | 2/2016 |
| RU | 2 386 954 C1 | 4/2010 |
| RU | 2 430 424 C1 | 9/2011 |
| WO | 2006/035035 A1 | 4/2006 |

OTHER PUBLICATIONS

International Search Report dated Nov. 18, 2016 received in International Application No. PCT/CN2016/095683.
Russian Decision on Grant dated May 15, 2017 received in Russian Application No. 2016138427.
Notice of Allowance dated Feb. 19, 2019 received in U.S. Appl. No. 15/278,435.
Office Action dated Jul. 26, 2018 received in U.S. Appl. No. 15/278,435.

* cited by examiner

METHOD AND SYSTEM FOR FAST INSPECTING VEHICLE BASED ON MEASURE LENGTHS

CROSS REFERENCE TO RELATED APPLICATION

This application is a divisional application of U.S. application Ser. No. 15/278,435 filed on Sep. 28, 2016, which claims benefit of Chinese Patent Application No. 201510884071.7, filed on Dec. 4, 2015, the contents of which are incorporated herein by reference.

TECHNICAL FIELD

The present disclosure generally relates to the technology field for fast inspecting a vehicle based on radiation scan, and more particularly, to a method and a system for fast inspecting a vehicle based on a device for measuring a length.

BACKGROUND

In the field of fast inspecting a vehicle based on radiation scan, the current trend is to inspect a subject vehicle while it is traveling, since it can significantly improve the efficiency of security inspection. However, due to the reason that radiation rays of high energy is harmful to human body, during inspection of the subject vehicle, the cab (i.e. the head portion of the vehicle) should be blocked from the rays, to prevent the high-energy radiation rays from being emitted to the driver.

Presently, a most commonly used method is detecting the position of the vehicle by a plurality of photoelectric switches or light curtains as well as ground sensor coils installed in the inspection channel, and when the cab has passed a beam emitting region of the radiation rays (i.e. scanning region of the radiation rays), the radiation-ray source is controlled to emit a beam to scan the compartment behind the cab. However, errors are often generated in determination by means of optical switches or light curtains, which imposes a high risk to the safety of the driver.

SUMMARY

In view of the above, the present disclosure provides a system and a method for fast inspecting a vehicle which can fast and accurately recognize a subject vehicle, and inspect the subject vehicle safely.

Additional aspects and advantages of the present disclosure will be partly set forth in the following description and partly become apparent from the description, or can be learned from practice of the present disclosure.

One aspect of the present disclosure provides a method for fast inspecting a vehicle, which is applied in a system for fast inspecting a vehicle. The method includes: when a subject vehicle enters an inspection region, measuring a first length and a second length of the subject vehicle; determining whether the first length is larger than or equal to a preset first length threshold and the second length is larger than or equal to a preset second length threshold; if the first length is larger than or equal to the first length threshold and the second length is larger than or equal to the second length threshold, determining whether a gap portion of the subject vehicle between a first portion and a second portion of the subject vehicle appears in a beam emitting region formed by a beam of radiation rays emitted by the system for fast inspecting a vehicle; and when the gap portion appears in the beam emitting region, emitting a beam of radiation rays of a first radiation dose to the subject vehicle according to the gap portion, wherein the subject vehicle moves with respect to the system for fast inspecting a vehicle.

Another aspect of the present disclosure provides a system for fast inspecting a vehicle, including: a radiation imaging device comprising a radiation-ray source configured to emit a beam of radiation rays for inspecting a subject vehicle; a detector configured to detect radiation rays transmitted through the subject vehicle and/or radiation rays scattered; and an image processing apparatus configured to form an image according to signals of the radiation rays detected by the detector; a length measuring device configured to measure a first length and a second length of the subject vehicle when the subject vehicle enters an inspection region; and a controlling device configured to determine whether the first length is larger than or equal to a preset first length threshold and the second length is larger than or equal to a preset second length threshold; if the first length is larger than or equal to the first length threshold and the second length is larger than or equal to the second length threshold, determine whether a gap portion of the subject vehicle between a first portion and a second portion of the subject vehicle appears in a beam emitting region formed by the beam of radiation rays; and when the gap portion appears at a finishing position of the beam emitting region, control the radiation imaging device to emit a beam of radiation rays of a first radiation dose to the subject vehicle according to the gap portion, wherein the subject vehicle moves with respect to the length measuring device.

Accordingly, in the method and the system for fast inspecting a vehicle provided by the present disclosure, lengths of portions of the subject vehicle are measured; when the lengths meet predetermined conditions, the gap portion of the subject vehicle can be detected. In this way, the timing for emitting a beam of radiation rays can be determined accurately, and it can avoid risk to the safety of the driver due to errors in determination of the head portion of the subject vehicle.

BRIEF DESCRIPTION OF THE DRAWINGS

The above and other features and advantages of the present disclosure will become apparent from exemplary embodiments thereof described in detail with reference to accompanying drawings.

DETAILED DESCRIPTION

Hereinafter, the exemplary embodiments will be described more fully with reference to the accompanying drawings. However, the exemplary embodiments can be implemented in various manners, and should not be understood as limited to the embodiments set forth herein. Instead, these embodiments are provided to make the present disclosure more thorough and complete, and to fully convey the concept of the exemplary embodiments to those skilled in the art. Throughout the accompanying drawings, like symbols represent like or the same structure, and thus the redundant description will be omitted.

The features, structure and characteristics described can be combined in one or more embodiments in any suitable way. In the following description, more specific details are provided to enable thorough understanding of the embodiments of the present disclosure. However, it should be appreciated by those skilled in the art that the technical solution of the present disclosure can be practiced without one or more of the particular details or can be practiced with other methods, components, and so on. In some cases, known structure or operation will not be illustrated in detail to avoid obscuration of the present disclosure.

Figure 1:
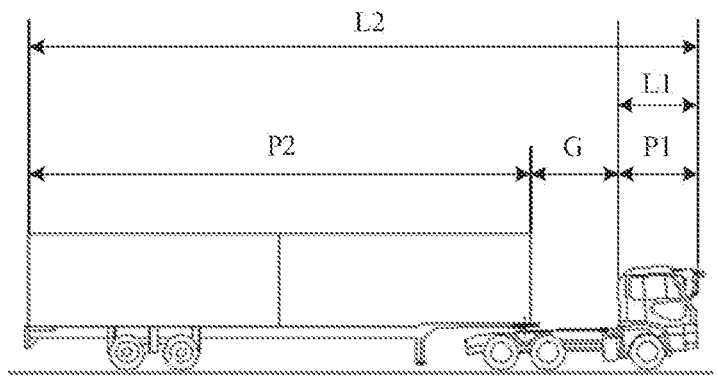
FIG. 1 is a side view of a subject vehicle according to an example.

FIG. 1 is a side view of a subject vehicle according to an example. As shown in FIG. 1, a subject vehicle 10, for example, a van with a compartment or a truck with a container, includes a first portion P1 (such as a cab, i.e. a head portion) a second portion P2 (such as a compartment portion), and a gap portion G between the first portion P1 and the second portion P2. For a truck with a container, generally, the gap portion G has a length of about 1 meter. For a van with a compartment, the gap portion G has a length between about several centimeters to dozens of centimeters.

In the method for fast inspecting a vehicle according to the present disclosure, the subject vehicle can move with respect to the system for fast inspecting the vehicle. In an embodiment, the subject vehicle can travel through a stationary system for fast inspecting the vehicle, or in another embodiment, the subject vehicle can be stationary and the system for fast inspecting the vehicle inspects the vehicle while the system is moving.

Generally, the method for fast inspecting a vehicle of the present disclosure will be described below with an example in which the subject vehicle travels through a stationary system for fast inspecting a vehicle.

Figure 2A:
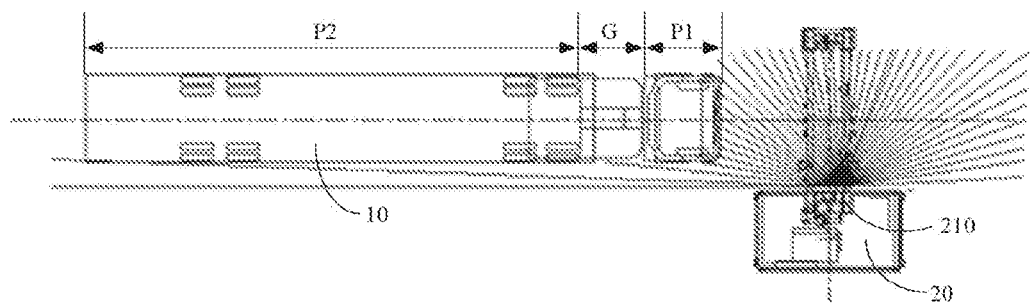
FIG. 2A and FIG. 2B are schematic diagrams showing a method for fast inspecting a vehicle in different operation states according to an exemplary embodiment.
Figure 2B:
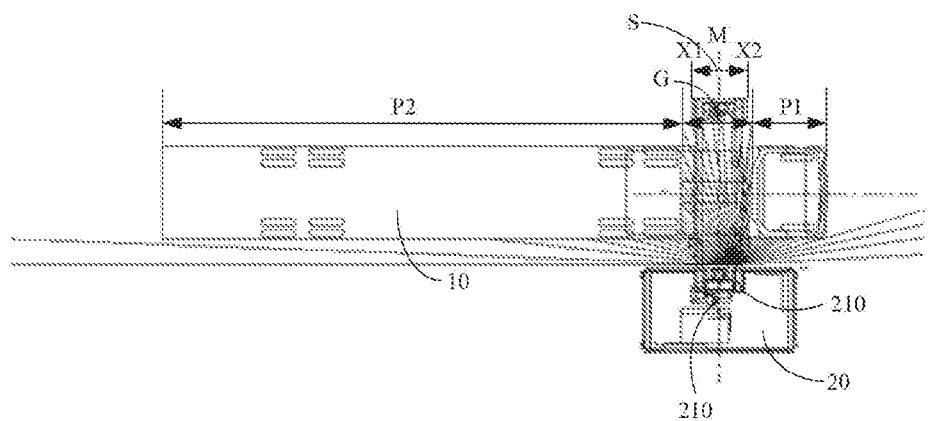
Figure 3:
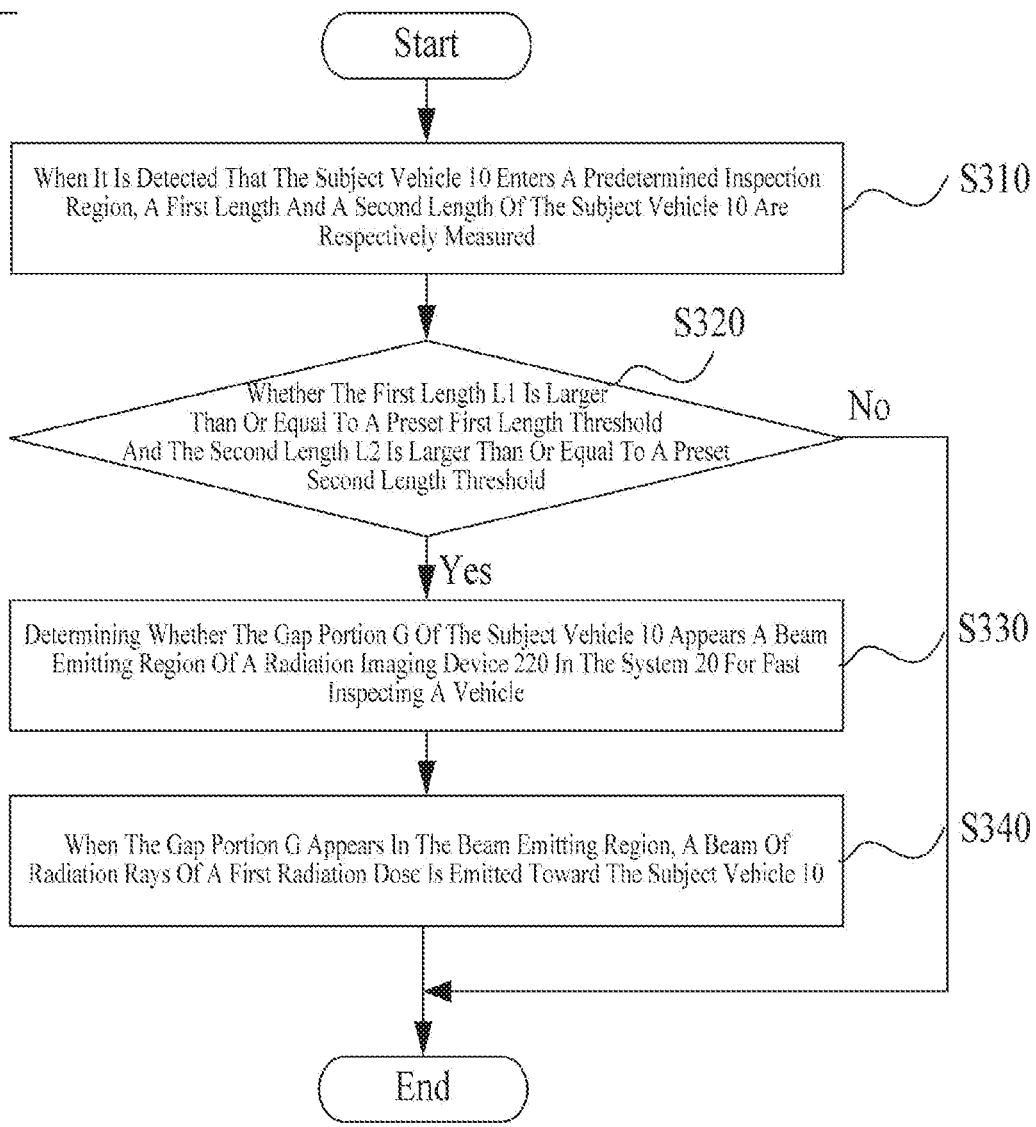
FIG. 3 is a flowchart illustrating a method for fast inspecting a vehicle according to an exemplary embodiment.

FIG. 2A and FIG. 2B are schematic diagrams showing a method for fast inspecting a vehicle in different operation states according to an exemplary embodiment. FIG. 3 is a flowchart illustrating a method for fast inspecting a vehicle according to an exemplary embodiment. With reference to FIGS. 2A, 2B and 3 together, the method 30 includes the following steps.

At step S310, when it is detected that the subject vehicle 10 enters a predetermined inspection region, a first length and a second length of the subject vehicle 10 are respectively measured.

Figure 4:
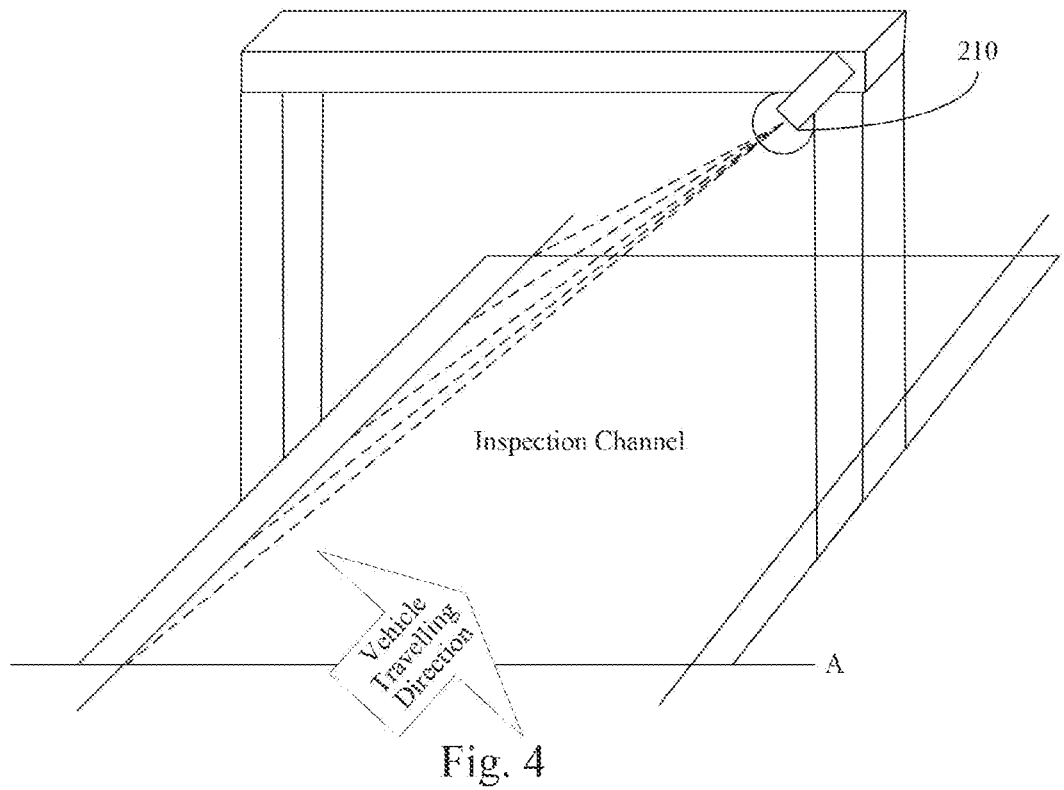
FIG. 4 is a schematic diagram showing a recognizable region of a laser scanner according to an example.

For example, a system 20 for fast inspecting a vehicle includes a device for measuring a length. The device for measuring a length includes for example, a laser scanner or a 3D imaging camera and the like. The system 20 for fast inspecting a vehicle measures the subject vehicle 10 entering a predetermined inspection region by utilizing the device for measuring a length. The predetermined inspection region can be a recognizable region of the device for measuring a length, for example. For example, the device for measuring a length is a laser scanner, and FIG. 4 is a schematic diagram showing a recognizable region of a laser scanner 210. As shown in FIG. 4, the laser scanner 210 can be disposed above a side of an inspection channel, in order to measure a width of the subject vehicle 10 in addition to a height and a length of the subject vehicle 10. Generally, the laser scanner 210 scans the subject vehicle 10 with laser at a preset scanning frequency, for example 100 Hz (i.e. 100 times of scanning per second). The laser scanner 210, at a time, emits a laser beam including a plurality of laser rays in different angles, and the plurality of laser rays form a plane which covers a range with a starting point A. The starting point A marks the beginning of the recognizable region of the laser scanner 210. The inspection region is also the recognizable region of the laser scanner 210. Alternatively, the laser scanner 210 can also be disposed on the top of the inspection channel.

The laser scanner as the device for measuring a length is easy to be installed and has a low cost. In practical application, there is no need to strictly follow the inclined angle of a sensor required by the installation rules. The inclined installation angle will not affect the desired accuracy and algorithm. In addition, the laser scanner has a wide detection range, and can continuously monitor a range with a length of 80 meters or even longer.

In another embodiment, the above device for measuring a length can also be a 3D imaging camera. In this case, a three-dimension image can be captured by the 3D imaging camera, in order to measure a length of the subject vehicle and other measurements.

In an embodiment, whether the subject vehicle 10 has entered the predetermined inspection region can be detected by a photoelectric switch, a light curtain, a laser sensor, a radar sensor or a laser scanner. If a laser scanner is used for such detection, the above laser scanner 210 for measuring the length of the subject vehicle can be used for this purpose, or an additional laser scanner can be installed to perform the detection.

Still referring to FIG. 2A, the subject vehicle 10 as a whole has entered the inspection region, that is, the whole part of the subject vehicle 10 has entered recognizable range of the laser scanner. The laser scanner 210 can continuously scan the subject vehicle 10 with laser at a predetermined scanning frequency. A two-dimension image of the subject vehicle 10 can be formed according to data acquired and returned by scanning the subject vehicle 10 with a laser beam emitted from the laser scanner 210. According to the two-dimension image of the subject vehicle 10, the first portion P1, the second portion P2 and the gap portion G of the subject vehicle 10 can be respectively recognized, and a length of each of the portions can be measured.

In some embodiments, as shown in FIG. 1, said first length is a length L1 of the first portion P1 of the subject vehicle 10, and said second length is a total length L2 of the subject vehicle 10, i.e. a total length of the first portion P1, the second portion P2 and the gap portion G of the subject vehicle 10.

In some embodiments, said first length is a length of the first portion P1 of the subject vehicle 10, and said second length can also be a length of the second portion P2 of the subject vehicle 10.

In some embodiments, the system 20 for fast inspecting a vehicle can also utilize a laser scanner to measure a width of the subject vehicle 10. In this case, when said device for measuring a length is a laser scanner, the laser scanner for measuring a width can be the same laser scanner as said laser scanner for measuring a length, or can be another laser scanner. For example, as shown by the laser scanner 210 which is configured for measuring both width and length in FIG. 4, when the laser scanner for measuring a width and the laser scanner for measuring a length are the same laser scanner 210, the laser scanner 210 can be disposed over a side (or on a side wall) of the inspection channel, in order to measure both of the length and the width of the subject vehicle 10.

Figure 6:
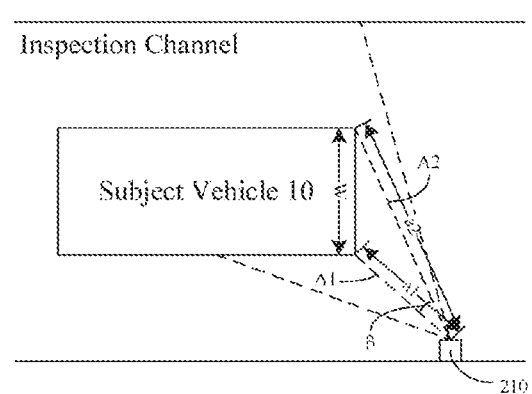
FIG. 6 is a schematic diagram showing width measurement with a laser scanner according to an example.

FIG. 6 is a schematic diagram showing the laser scanner 210 measuring the width W of the subject vehicle 10. As shown in FIG. 6, the laser scanner 210 can calculate the width W of the subject vehicle 10 according to a length a1 of a laser ray A1, a length a2 of a laser ray A2 and an angle β between the laser ray A1 and the laser ray A2. In addition, the measurement of the width can be a result of one measurement, or can be a fitted result (for example, an average) of combination of several measurements, and the present disclosure is not limited thereto.

At step S320, it is determined whether the first length is larger than or equal to a preset first length threshold and the second length is larger than or equal to a preset second length threshold, if the first length is larger than or equal to the first length threshold and the second length is larger than or equal to the second length threshold, the process of the method is turned to perform step S330, otherwise, the process of the method is ended.

By determining whether the first length and the second length exceed the preset thresholds, a vehicle with a gap portion G can be fast recognized. For example, the first length P1 is the length L1, and the second length is a total length L2. The length L1 of P1 is generally between 1.3 meters and 5.2 meters, and the total length L2 is generally between 5.4 meters and 18 meters. Therefore, the first length threshold can be set between 1.5 meters and 2.7 meters, and the second length threshold can be set between 6 meters and 10 meters. It should be noted that, these thresholds are merely for example, and the present disclosure is not limited thereto. The thresholds can be set according to practical requirements in application.

In some embodiments, before step S320, the method also includes: it is determined whether the width of the subject vehicle 10 is larger than a preset width threshold. If the width of the subject vehicle 10 is larger than the preset width threshold, the process of the method is turned to perform step S330; otherwise, the process of the method is ended.

In some embodiments, at step S320, in addition to determining whether the first length is larger than or equal to a preset first length threshold and the second length is larger than or equal to the second length threshold, it is also determined whether the width of the subject vehicle 10 is larger than a preset width threshold. If the first length is larger than or equal to the first length threshold and the second length is larger than or equal to the second length threshold, and the width of the subject vehicle 10 is larger than the width threshold, the process of the method is turned to perform step S330; otherwise, the process of the method is ended.

Generally, the width of the subject vehicle is between 1.5 meters and 3 meters. Therefore, the width threshold can be selected as between 1 meter and 1.5 meters. The present disclosure is not limited thereto.

By determining the width of the subject vehicle 10, it can effectively recognize whether an undesired moving object has entered the inspection channel, so as to prevent inspection radiation rays from emitting to such undesired moving object.

At step S330, it is determined whether the gap portion G of the subject vehicle 10 appears a beam emitting region of a radiation imaging device 220 in the system 20 for fast inspecting a vehicle.

As shown in FIG. 2B, the region S for emitting a beam of the radiation imaging device 220 is formed by a beam of radiation rays emitted by a radiation-ray source in the radiation imaging device 220. When seen from the traveling direction of the subject vehicle 10, the region S for emitting a beam includes a starting position X1 and a finishing position X2. In order for the subject vehicle 10 to receive a beam of radiation rays to be scanned, the subject vehicle 10 enters the region S for emitting a beam from the starting position X1 and exits the region S for emitting a beam at the finishing position X2.

At step S340, when the gap portion G appears in the beam emitting region, a beam of radiation rays of a first radiation dose is emitted toward the subject vehicle 10.

Still referring to FIG. 2B, the first portion P1 of the subject vehicle 10 has passed the finishing position X2 of the region S for emitting a beam, and a front edge of the gap portion G appears at the finishing position X2 of the region S for emitting a beam of the radiation imaging device 220. At this time, a controlling device (not shown in the figure) in the system 20 for fast inspecting a vehicle is configured to control the radiation imaging device 220 to emit a beam of radiation rays of the first radiation dose toward the subject vehicle 10.

In some embodiments, the method also includes emitting a beam of radiation rays of a second radiation dose toward the first portion P1 of the subject vehicle 10. The second radiation dose is a radiation dose which is safe for a human body. It should be noted that the specific value of the second radiation dose is not limited in the present disclosure, and in application, it can be determined depending on criteria of various countries and districts. The first radiation dose is higher than the second radiation dose.

In some embodiments, at the time when the front edge of the gap portion G appears at the finishing position X2 of the region S for emitting a beam of the radiation imaging device 220, the controlling device is configured to control the radiation imaging device 220 to emit a beam of radiation rays of the first radiation dose toward the subject vehicle 10.

In some embodiments, in order to better safeguard the driver, the controlling device can also be configured to control the radiation imaging device 220 to emit a beam of radiation rays of the first radiation dose toward the subject vehicle 10 at a predetermined time after the front edge of the gap portion G appears at the finishing position X2 of the region S for emitting a beam of the radiation imaging device 220.

The predetermined time can be determined according to a predetermined distance and a relative moving speed of the subject vehicle 10 with respect to the system 20 for fast inspecting a vehicle. The predetermined distance can be set depending on specific implementation, for example. The relative moving speed of the subject vehicle 10 with respect to the system 20 for fast inspecting a vehicle can be measured by a speed radar for example, or can be measured by the same laser scanner 210.

To determine the time when the front edge of the gap portion G appears at the finishing position X2 of the region S for emitting a beam, it can be determined whether the front edge of the gap portion G has reached the finishing position X2 according to a change in depth from the first portion P1 (i.e. the head portion) and the gap portion G For example, when the first portion P1 has not passed the finishing position X2, the rays at the finishing position X2 will be emitted on the first portion P1, and a distance value acquired and returned will be relatively small. When the first portion P1 has passed the finishing position X2, the rays at the finishing position X2 will be emitted on the gap portion G, and a distance value acquired and returned will be relatively large. Based on this, it can be determined whether the front edge of the gap portion G has reached the finishing position X2. For example, it can be determined based on a difference value between the two distance values returned. That is, if the distance values change from a relatively small value to a relatively large value, and an absolute value of the difference value is larger than a preset first threshold, it can be determined that the front edge of the gap portion has passed the finishing position X2. The first threshold can be set depending on requirements of practical application, and the present disclosure is not limited thereto.

In some embodiments, the controlling device can be configured to control the radiation imaging device 220 to emit a beam of radiation rays toward the subject vehicle 10 at a time when a rear edge of the gap portion G passes the finishing position X2 of the region S for emitting a beam of the radiation imaging device 220.

To determine the time when the rear edge of the gap portion G passes the finishing position X2 of the region S for emitting a beam of the radiation imaging device 220, it can be determined whether the rear edge of the gap portion has passed the finishing position X2 according to a change in depth from the gap portion G and the second portion P2 (i.e. the compartment portion). For example, when the gap portion G has not passed the finishing position X2, the rays at the finishing position X2 will be emitted on the gap portion G, and a distance value acquired and returned will be relatively large. When the gap portion G has passed the finishing position X2, the rays at the finishing position X2 will be emitted on the second portion P2, and a distance value acquired and returned will be relatively small. Based on this, it can be determined whether the rear edge of the gap portion G has passed the finishing position X2. For example, it can be determined based on a difference value between the two distance values returned. That is, if the distance values change from a relatively large value to a relatively small value, and an absolute value of the difference value is larger than a preset second threshold, it can be determined that the rear portion of the gap portion has passed the finishing position X2. The second threshold can be set depending on requirements of practical application, and the present disclosure is not limited thereto.

Accordingly, in the method for fast inspecting a vehicle provided by the present disclosure, lengths of portions of the subject vehicle are measured; when the lengths meet predetermined conditions, the gap portion of the subject vehicle can be detected. In this way, the timing for emitting a beam of radiation rays can be determined accurately, and it can avoid risk to the safety of the driver due to errors in determination of the head portion of the subject vehicle.

In addition, in the method for fast inspecting a vehicle provided by the present disclosure, the width of the subject vehicle can also be measure. In this way, it can recognize object to be inspected in the inspection channel. An object other than a vehicle can be effectively recognized and excluded according to the width. Therefore, it can reduce a probability of mistakes in determination and it can improve the safety level.

Figure 5:
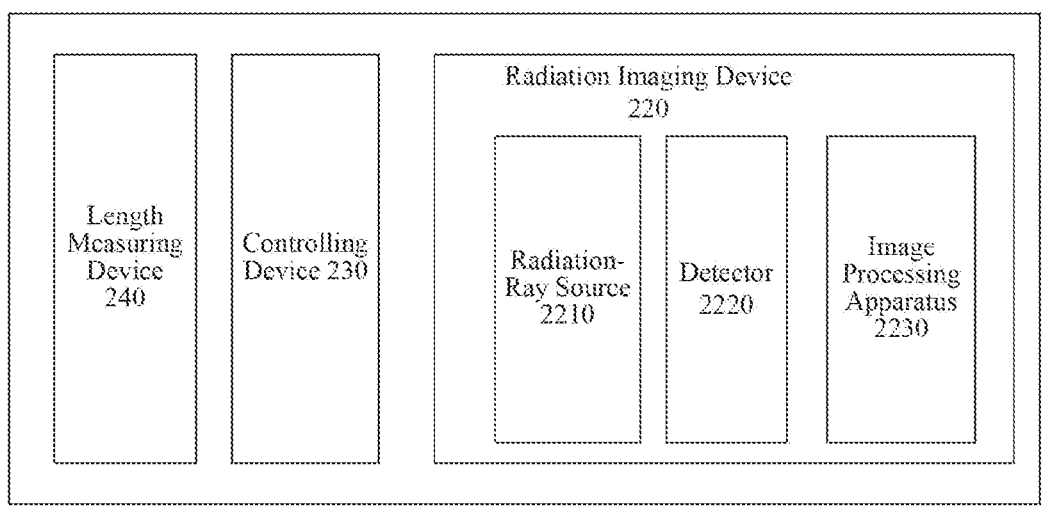
FIG. 5 is a block diagram illustrating a system for fast inspecting a vehicle according to an exemplary embodiment.

FIG. 5 is a block diagram illustrating a system for fast inspecting a vehicle according to an exemplary embodiment. As shown in FIG. 5, the system 20 for fast inspecting a vehicle includes a length measuring device 240, a radiation imaging device 220 and a controlling device 230.

The radiation imaging device 220 includes a radiation-ray source 2210, a detector 2220 and an image processing apparatus 2230. The radiation-ray source 2210 is configured to emit a beam of radiation rays to a subject vehicle passing through the inspection channel. The beam of radiation rays can be all kinds of rays which can image an object by means of radiation, such as X rays, γ rays, neutrons and the like, and the present disclosure is not limited thereto. The radiation-ray source 2210 can include for example an X-ray machine, an accelerator, a neutron generator and the like. The radiation-ray source 2210 can emit a beam of radiation rays under control of the controlling device 230, for example, by receiving a controlling signal of the controlling device 230. The radiation-ray source 2210 can emit or stop emitting a beam of radiation rays by opening or closing a mechanical shutter. The detector 2220 is configured to detect radiation rays transmitted through the subject vehicle and/or radiation rays scattered. The image processing apparatus 2230 is configured to form an image according to signals of the radiation rays detected by the detector 2220, to inspect the internal part of the subject vehicle.

The length measuring device 240 is configured to measure the first length and the second length of the subject vehicle when the subject vehicle enters the inspection region. The inspection region has been described in the above, which will not be repeated herein. The length measuring device 240 can include, for example, a laser scanner or a 3D imaging camera and the like. When the length measuring device 240 is the laser scanner 210 as shown in FIGS. 2A and 2B, the length measuring device 210 can be disposed at above a side of an inspection channel, or can also be disposed on the top of the inspection channel, as shown in FIG. 4. In an optional embodiment, a distance between the laser scanner 210 and a central position M of the beam emitting region which is formed by the beam of radiation rays emitted by the radiation imaging device 220 is smaller than or equal to 1 meter. The measurement of lengths by the laser scanner 210 has been described in the above, which will not be repeated herein.

The laser scanner as the device for measuring a length is easy to be installed and has a low cost. In practical application, there is no need to strictly follow the inclined angle of a sensor required by the installation rules. The inclined installation angle will not affect the desired accuracy and algorithm. In addition, the laser scanner has a wide detection range, and can continuously monitor a range with a length of 80 meters or even longer.

A 3D imaging camera can also be used for measuring a length. In this case, a three-dimension image can be firstly captured by the 3D imaging camera, and then lengths can be measured according to the captured three dimensional image.

In addition, the system 20 for fast inspecting a vehicle can also include a photoelectric switch, a light curtain, a laser sensor, a radar sensor or the like, for detecting whether the subject vehicle has enters the inspection region. In some embodiments, as shown in FIG. 1, said first length is a length L1 of the first portion P1 of the subject vehicle 10, and said second length is a total length L2 of the subject vehicle 10, i.e. a total length of the first portion P1, the second portion P2 and the gap portion G of the subject vehicle 10.

In some embodiments, said first length is a length of the first portion P1 of the subject vehicle 10, and said second length can also be a length of the second portion P2 of the subject vehicle 10.

The controlling device 230 is configured to determine whether the first length is larger than or equal to a preset first length threshold and the second length is larger than or equal to the second length threshold, and if the first length is larger than or equal to the first length threshold and the second length is larger than or equal to the second length threshold, it can be determined whether the gap portion G of the subject vehicle appears in the beam emitting region of the radiation imaging device 220. When the gap portion G appears in the beam emitting region, a beam of radiation rays can be emitted toward the subject vehicle based on the gap portion G The first length threshold and the second length threshold have been described in the above, which will not be repeated herein.

The controlling device 230 can fast recognize a vehicle with a gap portion G by determining whether the first length and the second length exceed the preset thresholds.

In some embodiments, the system 20 for fast inspecting a vehicle can also include a laser scanner configured to measure a width of the subject vehicle 10 when the subject vehicle 10 enters the predetermined inspection region. When the length measuring device 240 is also a laser scanner, the laser scanner for measuring a width of the subject vehicle 10 can be the same laser scanner as said laser scanner for measuring a length, or can be another laser scanner. For example, as shown by the laser scanner 210 which is configured for measuring both width and length in FIG. 4, when the laser scanner for measuring a width and the laser scanner for measuring a length are the same laser scanner 210, the laser scanner 210 can be disposed over a side (or on a side wall) of the inspection channel, in order to measure both of the length and the width of the subject vehicle 10. The measurement of the width of the subject vehicle 10 by the laser scanner 210 when the subject vehicle 10 enters the predetermined inspection channel has been described in the above, which will not be repeated herein.

In some embodiments, the controlling device 230 is configured to, before it is determined whether the first length is larger than or equal to a preset first length threshold and the second length is larger than or equal to a preset second length threshold, it is determined whether the width of the subject vehicle 10 is larger than a preset width threshold. If the width of the subject vehicle 10 is larger than the width threshold, the length measuring device 240 is instructed to measure said first length and the second length and it is determined whether the first length is larger than or equal to a preset first length threshold and the second length is larger than or equal to a preset second length threshold. The width threshold has been described in the above, which will not be repeated herein.

In some embodiments, the controlling device 230 is configured to, in addition to determining whether the first length is larger than or equal to a preset first length threshold and the second length is larger than or equal to the second length threshold, it is also determined whether the width of the subject vehicle 10 is larger than a preset width threshold. If the first length is larger than or equal to the first length threshold and the second length is larger than or equal to the second length threshold, and the width of the subject vehicle 10 is larger than the width threshold, it is determined whether the gap portion G of the subject vehicle appears in the beam emitting region of the radiation imaging device 220. The width threshold has been described in the above, which will not be repeated herein.

In the example below, the length measuring device 240 is still the laser scanner 210 as shown in FIG. 4. Still referring to FIG. 2B, the region S for emitting a beam is formed by a beam of radiation rays emitted. When seen from the traveling direction of the subject vehicle 10, the region S for emitting a beam includes a starting position X1 and a finishing position X2. In order for the subject vehicle 10 to receive a beam of radiation rays to be scanned, the subject vehicle 10 enters the region S for emitting a beam from the starting position X1 and exits the region S for emitting a beam at the finishing position X2.

As shown in FIG. 2B, when the first portion P1 of the subject vehicle 10 has passed the finishing position X2 of the region S for emitting a beam, and a front edge of the gap portion G appears at the finishing position X2 of the region S for emitting a beam, the controlling device 230 can be configured to control the radiation imaging device 220 to emit a beam of radiation rays of a first radiation dose toward the subject vehicle 10.

In some embodiments, before determination of the gap portion G, the controlling device 230 is also configured to control the radiation imaging device 20 to emit a beam of radiation rays of a second radiation dose to the first portion P1 of the subject vehicle 10. The second radiation dose is a radiation dose which is safe for a human body. It should be noted that the specific value of the second radiation dose is not limited in the present disclosure, and in application, it can be determined depending on criteria of various countries and districts. The first radiation dose is higher than the second radiation dose.

In some embodiments, at the time when the front edge of the gap portion G appears at the finishing position X2 of the region S for emitting a beam of the radiation imaging device 220, the controlling device 230 is configured to control the radiation imaging device 220 to emit a beam of radiation rays of the first radiation dose toward the subject vehicle 10.

In some embodiments, in order to better safeguard the driver, the controlling device 230 can also be configured to control the radiation imaging device 220 to emit a beam of radiation rays of the first radiation dose toward the subject vehicle 10 at a predetermined time after the front edge of the gap portion G appears at the finishing position X2 of the region S for emitting a beam of the radiation imaging device 220.

The predetermined time can be determined according to a predetermined distance and a relative moving speed of the subject vehicle 10 with respect to the system 20 for fast inspecting a vehicle. The predetermined distance can be set depending on specific implementation, for example. The relative moving speed of the subject vehicle 10 with respect to the system 20 for fast inspecting a vehicle can be measured by a speed radar for example, or can be measured by the same laser scanner 210.

To determine the time when the front edge of the gap portion G appears at the finishing position X2 of the region S for emitting a beam, it can be determined whether the front edge of the gap portion G has reached the finishing position X2 according to a change in depth from the first portion P1 (i.e. the head portion) and the gap portion G For example, when the first portion P1 has not passed the finishing position X2, the rays at the finishing position X2 will be emitted on the first portion P1, and a distance value acquired and returned will be relatively small. When the first portion P1 has passed the finishing position X2, the rays at the finishing position X2 will be emitted on the gap portion G, and a distance value acquired and returned will be relatively large. Based on this, it can be determined whether the front edge of the gap portion G has reached the finishing position X2. For example, it can be determined based on a difference value between the two distance values returned. That is, if the distance values change from a relatively small value to a relatively large value, and an absolute value of the difference value is larger than a preset first threshold, it can be determined that the front edge of the gap portion has passed the finishing position X2. The first threshold can be set depending on requirements of practical application, and the present disclosure is not limited thereto.

In some embodiments, the controlling device 230 can be configured to control the radiation imaging device 220 to emit a beam of radiation rays toward the subject vehicle 10 at a time when a rear edge of the gap portion G passes the finishing position X2 of the region S for emitting a beam of the radiation imaging device 220.

To determine the time when the rear edge of the gap portion G passes the finishing position X2 of the region S for emitting a beam of the radiation imaging device 220, it can be determined whether the rear edge of the gap portion has passed the finishing position X2 according to a change in depth from the gap portion G and the second portion P2 (i.e. the compartment portion). For example, when the gap portion G has not passed the finishing position X2, the rays at the finishing position X2 will be emitted on the gap portion G, and a distance value acquired and returned will be relatively large. When the gap portion G has passed the finishing position X2, the rays at the finishing position X2 will be emitted on the second portion P2, and a distance value acquired and returned will be relatively small. Based on this, it can be determined whether the rear edge of the gap portion G has passed the finishing position X2. For example, it can be determined based on a difference value between the two distance values returned. That is, if the distance values change from a relatively large value to a relatively small value, and an absolute value of the difference value is larger than a preset second threshold, it can be determined that the rear portion of the gap portion has passed the finishing position X2. The second threshold can be set depending on requirements of practical application, and the present disclosure is not limited thereto.

Accordingly, in the system for fast inspecting a vehicle provided by the present disclosure, lengths of portions of the subject vehicle are measured; when the lengths meet predetermined conditions, the gap portion of the subject vehicle can be detected. In this way, the timing for emitting a beam of radiation rays can be determined accurately, and it can avoid risk to the safety of the driver due to errors in determination of the head portion of the subject vehicle.

In addition, in the system for fast inspecting a vehicle provided by the present disclosure, the width of the subject vehicle can also be measure. In this way, it can recognize object to be inspected in the inspection channel. An object other than a vehicle can be effectively recognized and excluded according to the width. Therefore, it can reduce a probability of mistakes in determination and it can improve the safety level.

The exemplary embodiments of the present disclosure have been specifically illustrated and described above. It should be understood that, the present disclosure is not limited to the embodiments disclosed. Instead, the present disclosure intends to cover all the alteration and equivalent replacement within the scope of the appending claims.

What is claimed is:

1. A method for fast inspecting a vehicle, which is applied in a system for fast inspecting a vehicle, the method comprising:

step (a), when a subject vehicle enters an inspection region, measuring a first length and a second length of the subject vehicle;

step (b), determining whether the first length is larger than or equal to a preset first length threshold and the second length is larger than or equal to a preset second length threshold;

step (c), if the first length is larger than or equal to the first length threshold and the second length is larger than or equal to the second length threshold, determining whether a gap portion of the subject vehicle between a first portion and a second portion of the subject vehicle appears in a beam emitting region formed by a beam of radiation rays emitted by the system for fast inspecting a vehicle; and step (d), when the gap portion appears in the beam emitting region, emitting a beam of radiation rays of a first radiation dose to the subject vehicle according to the gap portion, wherein the subject vehicle moves with respect to the system for fast inspecting a vehicle.

2. The method for fast inspecting a vehicle according to claim 1, wherein before the step (a), the method further comprises:

when the subject vehicle enters the inspection region, measuring a width of the subject vehicle;

determining whether the width of the subject vehicle is larger than a preset width threshold; and if the width of the subject vehicle is larger than the width threshold, performing the steps (a) to (d).

3. The method for fast inspecting a vehicle according to claim 1, wherein the step (a) further comprises: when the subject vehicle enters the inspection region, measuring a width of the subject vehicle;

the step (b) further comprises: determining whether the width of the subject vehicle is larger than a preset width threshold; and the step (c) further comprises: if the first length is larger than or equal to the first length threshold, the second length is larger than or equal to the second length threshold, and the width of the subject vehicle is larger than the width threshold, determining whether a gap portion of the subject vehicle between a first portion and a second portion of the subject vehicle appears in the beam emitting region.

4. The method for fast inspecting a vehicle according to claim 1, wherein the first length is a length of the first portion of the subject vehicle, and the second length is a sum of lengths of the first portion, the second portion and the gap portion of the subject vehicle; or the first length is a length of the first portion of the subject vehicle, and the second length is a length of the second portion of the subject vehicle.

5. The method for fast inspecting a vehicle according to claim 1, wherein emitting a beam of radiation rays of a first radiation dose to the subject vehicle according to the gap portion comprises: determining an appearing time when the gap portion appears at a finishing position of the beam emitting region, and emitting the beam of radiation rays of the first radiation dose to the second portion of the subject vehicle at the determined appearing time.

6. The method for fast inspecting a vehicle according to claim 5, wherein determining an appearing time when the gap portion appears at a finishing position of the beam emitting region comprises: continuously detecting data returned by the radiation rays at the finishing position of the beam emitting region, determining whether an absolute value of a difference in a change in the returned data from a first value to a second value is larger than a preset first threshold, the first value being smaller than the second value, determining a time when the change occurred, wherein the determined time is determined as the appearing time.

7. The method for fast inspecting a vehicle according to claim 1, wherein emitting a beam of radiation rays of a first radiation dose to the subject vehicle according to the gap portion comprises: determining an appearing time when the gap portion appears at a finishing position of the beam emitting region, and emitting the beam of radiation rays of the first radiation dose to the second portion of the subject vehicle at a predetermined time after the determined appearing time.

8. The method for fast inspecting a vehicle according to claim 7, wherein the predetermined time is determined according to a predetermined distance and a relative moving speed of the subject vehicle with respect the system for fast inspecting a vehicle.

9. The method for fast inspecting a vehicle according to claim 1, wherein emitting a beam of radiation rays of a first radiation dose to the subject vehicle according to the gap portion comprises: determining a leaving time when the gap portion leaves the finishing position of the beam emitting region, and emitting the beam of radiation rays of the first radiation dose to the subject vehicle at the determined leaving time.

10. The method for fast inspecting a vehicle according to claim 9, wherein determining a leaving time when the gap portion leaves the finishing position of the beam emitting region comprises: continuously detecting data returned by the radiation rays at the finishing position of the beam emitting region, determining whether an absolute value of a difference in a change in the returned data from a first value to a second value is larger than a preset second threshold, the first value being larger than the second value, determining a time when the change occurred, wherein the determined time is determined as the leaving time.

* * * * *